United States Patent
Heilmayer et al.

(10) Patent No.: US 10,913,703 B2
(45) Date of Patent: Feb. 9, 2021

(54) PURIFICATION OF PLEUROMUTILIN

(71) Applicant: NABRIVA THERAPEUTICS GMBH, Vienna (AT)

(72) Inventors: Werner Heilmayer, Zillingtal (AT); Lee Spence, Vienna (AT); Peter Hinsmann, Vienna (AT)

(73) Assignee: NABRIVA THERAPEUTICS GMBH, Vienna (AT)

( * ) Notice: Subject to any disclaimer, the term of this patent is extended or adjusted under 35 U.S.C. 154(b) by 0 days.

(21) Appl. No.: 16/482,809

(22) PCT Filed: Feb. 9, 2018

(86) PCT No.: PCT/EP2018/053314
§ 371 (c)(1),
(2) Date: Aug. 1, 2019

(87) PCT Pub. No.: WO2018/146264
PCT Pub. Date: Aug. 16, 2018

(65) Prior Publication Data
US 2020/0231529 A1    Jul. 23, 2020

(30) Foreign Application Priority Data
Feb. 10, 2017   (EP) .................................. 17155542

(51) Int. Cl.
*C07C 67/52*   (2006.01)
*C07C 69/013*   (2006.01)

(52) U.S. Cl.
CPC ............ *C07C 67/52* (2013.01); *C07C 69/013* (2013.01); *C07C 2603/36* (2017.05)

(58) Field of Classification Search
CPC .... C07C 67/52; C07C 2603/36; C07C 69/013
See application file for complete search history.

(56) References Cited

FOREIGN PATENT DOCUMENTS

| CN | 10183199 | * | 9/2010 | ............. C07C 67/56 |
| CN | 101838199 | | 1/2013 | |

OTHER PUBLICATIONS

Stieger et al., Chapter 7: "Recrystallization of active Pharmaceutical ingredients", (2012), p. 183-204.*
International Search Reported issued in PCT/EP2018/053314 dated Nov. 4, 2018.
Written Opinion of the International Searching Authority issued in PCT/EP2018/053314 dated Nov. 4, 2018.

* cited by examiner

*Primary Examiner* — Yong L Chu
(74) *Attorney, Agent, or Firm* — Workman Nydegger

(57) ABSTRACT

The present invention relates to purification methods of pleuromutilin (I) by means of crystallisation and/or recrystallisation. The process according to the present invention is carried out in the presence of i-propylacetate.

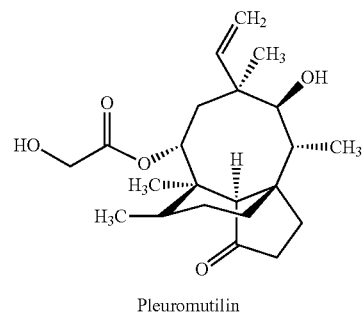

Pleuromutilin

20 Claims, No Drawings

PURIFICATION OF PLEUROMUTILIN

The present invention concerns purification methods of pleuromutilin which is used as starting material in the preparation of pharmaceutical active compounds. Specifically the described methods reduce 2,3-pleuromutiline epoxide which was discovered by the present inventors to be a critical impurity in pleuromutilin, and improve the overall purity of the material.

Pleuromutilin, a compound of formula

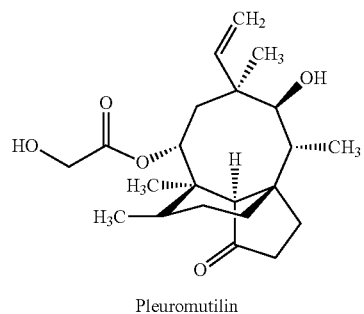 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin is a naturally occurring antibiotic, produced e.g. by the basidiomycetes *Pleurotus mutilus* and *P. passeckerianus*, see e.g. The Merck Index, 12th edition, item 7694.

Pleuromutilin is manufactured by a fermentation process, extracted from the fermentation broth and finally isolated as crystalline solid compound.

Pleuromutilin is used as starting material in the approved veterinary products tiamulin and valnemulin.

Pharmaceutical active compounds derived from pleuromutilin (semi synthetic compounds) are inhibitors of ribosomal protein synthesis in bacteria. The only representatives of approved semisynthetic pleuromutilins for human use is retapamulin (AltargoP®, AltabaxP®), a topical agent approved for short term treatment of impetigo and infected small lacerations, abrasions or sutured wounds. Tiamulin (Denagard®) and Valnemulin (Econor®), two other semi-synthetic pleuromutilin derivatives, have been used systemically in veterinary medicine for many years.

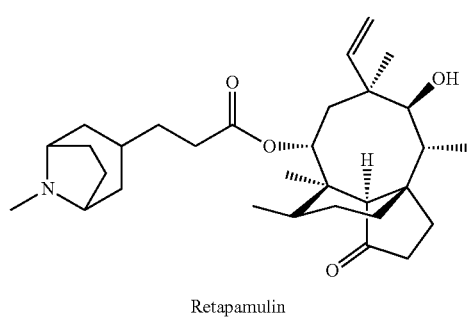

Retapamulin

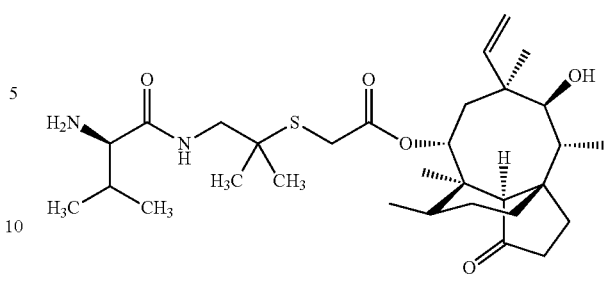

Valenmulin

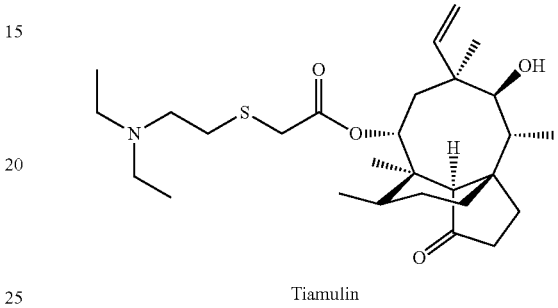

Tiamulin

Increasing rates of antibiotic resistance, in combination with the emergence of highly virulent pathogens like methicillin resistant *Staphylococcus aureus* (MRSA) and multi-drug resistant *Streptococcus pneumoniae*, underpin the urgent need of novel antibacterial agents suitable to combat serious bacterial infections caused by resistant organisms. Given their significant impact on morbidity and mortality, multi-drug resistant microbes are considered a substantial threat to public health by national academies, task forces including the Infectious Diseases Society of America, Centers for Disease Control and the World Health Organization.

Semi synthetic compounds derived from pleuromutilin have shown excellent activity against resistant organisms which include inter alia *Streptococcus pneumoniae, Haemophilus influenzae, Staphylococcus aureus* (including MRSA), *Moraxella catarrhalis, Legionella pneumophila, Chlamydophila pneumoniae* and *Mycoplasma pneumoniae*.

Two principal classes of semisynthetic pleuromutilins are known: sulfanylacetyl-mutilins and carbamoyloxy-mutilins. The difference is the different linker part from the tricyclic mutilin core to the side R.

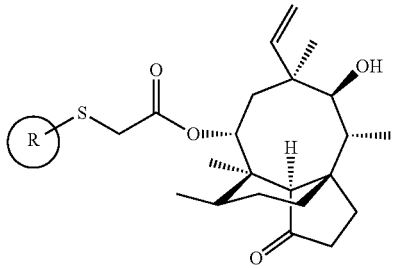

Sulfanyl-actelylmutilins

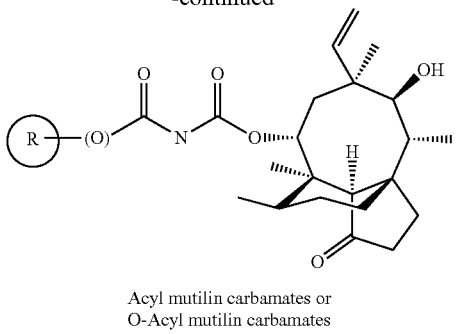

Acyl mutilin carbamates or
O-Acyl mutilin carbamates

Sulfanylacetyl-mutilins are inter alia disclosed in WO2005023257, WO1999021855, WO01/09095, WO02/04414, WO02/22580, WO03/082260, WO03/090740, WO2004011431, WO2007/000001, WO2007000004, WO2007014409, WO2007/079515, WO/2008/040043, WO 2008/113089, WO2009/009812, WO2009/009813, WO2010/025482, WO2011/146953, WO2011/146954, WO2012/031307, WO2015/110481, and carbamoyloxy-mutilins are disclosed inter alia in WO1997025309, WO1998005659, WO2006063801, WO2006099196, WO07062333, WO07062335. Both sulfanylacetyl- and carbamoyloxy-mutilins are using pleuromutilin as starting material.

A number of further pleuromutilins having the principle ring structure of pleuromutilin and being substituted at the primary hydroxy group have been developed, e.g. as antimicrobials.

Due to their pronounced antimicrobial activity, a group of pleuromutilin derivatives, amino-hydroxy-substituted cyclohexylsulfanylacetylmutilins, as disclosed in WO 2008/113089, have been found to be of particular interest. As described in WO2008/113089, 14-O-{[(4-Amino-2-hydroxy-cyclohexyl)-sulfanyl]-acetyl}-mutilins are particularly useful compounds because of their activity against Gram-positive and Gram-negative pathogens, especially in context of respiratory tract and skin and skin structure infections. In particular, 14-O-{[(1R, 2R, 4R)-4-amino-2-hydroxy-cyclohexylsulfanyl]-acetyl}-mutilin (in the following referred to as "BC-3781" or "lefamulin") has been developed for systemic use to treat serious infections in humans. BC-3781 has been inter alia described by R. Novak, Are pleuromutilin antibiotics finally fit for human use?, Ann. N.Y. Acad. Sci. 1241 (2011) 71-81 and W. T. Prince et al, Phase II Clinical Study of BC-3781, a Pleuromutilin Antibiotic, in Treatment of Patients with Acute Bacterial Skin and Skin Structure Infections, Antimicrobial Agents and Chemotherapy Vol 57, No 5 (2013), 2087-2094. The latter publication illustrates the first proof of concept of a pleuromutilin derivative to treat serious infections in humans via systemic administration. Also in the synthesis of BC-3781, pleuromutilin is used as starting material.

In the prior art, the following methods are described for the crystallisation/purification of pleuromutilin:

| Prior art | purification/crystallisation solvents described |
|---|---|
| WO2004/015122 | toluene, ethylacetate/heptane, methyl-isobutylketone/heptane |
| CN102703538 | methanol, ethanol, methyl-t-butylether |
| CN102633642 | acetone, methanol, petrolether |
| CN102351698 | methanol, ethanol, n-propanol, i-propylalcohol, t-butanol, dioxane, tetrahydrofuran (THF), dimethylformamide (DMF), dimethyl sulfoxide (DMSO), ethylacetate, methyl-isobutylketone, dichloromethane |
| CN102050737 | ethylether |
| CN101838199 | butylacetate |
| CN101676257 | methyl-isobutylketone |
| BG105074 | methyl-isobutylketone, methyl-t-butylketone |
| BE864361 | chloroalkanes |

Moreover, methods for the extraction and subsequent purification of pleuromutilin are disclosed in U.S. Pat. Nos. 4,092,424, 4,129,721, 4,247,542, GB patent 1,197,942 and published in papers such as Antibiotic Substances from Basidiomycetes VIII, F. Kavanagh et al., Proc. N.A.S., 1951, 570-574. The methods include extraction of the filtered broth with a water immiscible solvent e.g. toluene, ethyl acetate or chloroform. Extractions of pleuromutilins from the culture mycelium with a water miscible solvent, for example acetone, followed by extraction with a water immiscible solvent, for example ethyl acetate, are also described.

However, in none of the prior art documents the reduction of 2,3-pleuromutilin epoxide impurity is described. 2,3-pleuromutilin was found by the inventors of the present invention to be an important impurity of commercially available pleuromutilin. 2,3-pleuromutilin epoxide is mentioned in Eur. Congr. Biotechnol., $3^{rd}$, Volume 1, 1984, p 533-542 by N. Palma et al, as one of principal possible metabolites in pleuromutilin when produced by submerged culture of the Basidiomycetous Genus *Clitopilus* Kummer.

Another important impurity of pleuromutilin is 14-acetyl mutilin which, however, is much less critical in the further down stream chemistry. For example performing a tosylation reaction, which is often used to activate the primary hydroxy group in the pleuromutilin for the synthesis of semi-synthetic pleuromutlin derivatives (e.g. described in WO/2008/040043, WO 2008/113089, WO2009/009812, WO2009/009813, WO2010/025482, WO2011/146953, WO2011/146954, WO2012/031307, WO2015/110481), will completely remove 14-Acetylmutilin from a commercial batch. 14-acetylmutilin is not undergoing the tosylation reaction and is depleted as is in the mother liquor.

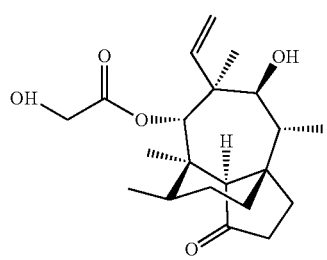

Tosylchloride

-continued

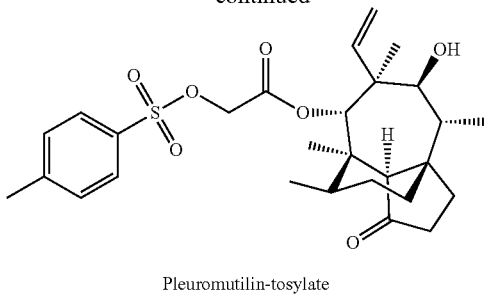

Pleuromutilin-tosylate

However, 2,3-pleuromutilin epoxide will undergo the tosylation reaction and is remaining in the isolated pleuromutilin tosylate.

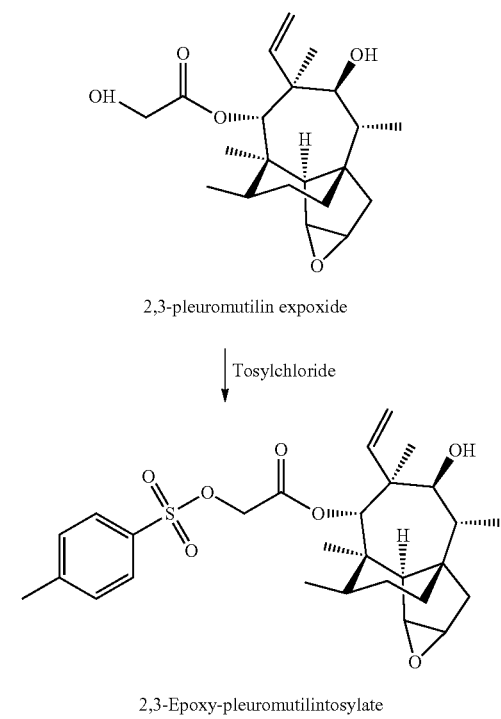

2,3-Epoxy-pleuromutilintosylate

Performing a tosylation reaction on a commercial pleuromutilin batch with a purity profile shown below without further purification and isolating the crystalline pleuromutilin tosylate leads to the following result:

| Purity of commercial pleuromutilin batch | Area % in HPLC | Purity after tosylation of commercial pleuromutilin batch | Area % in HPLC |
| --- | --- | --- | --- |
| Pleuromutilin | 86.17 | Pleuromutilin-tosylate | 98.55 |
| 14-Acetylmutilin | 5.56 | 14-Acetylmutilin | Not detected |
| 2,3-pleuromutilin epoxide | 0.31* | 2,3-Epoxy-pleuromutilintosylate | 1.32 |
| Total impurities | 13.83 | Total impurities | 1.44 |

*corresponds to 0.96% w/w after RRF (Relative Response Factor) correction

The purity of the isolated crystalline pleuromutilin-tosylate is improved from 86.17% area in the pleuromutilin to 98.55% area with no 14-acetylmutilin detected. However, the 2,3-pleuromutilin epoxide is converted to the 2,3-epoxy-pleuromutilintosylate and remains in the pleuromutilin tosylate as significant impurity. The RRF of 2,3-epoxy-pleuromutilintosylate, compared to pleuromutilin-tosylate, is about 1 for the wavelength used in the HPLC analysis method, translating the impurity to about 1.32% w/w. These data confirm that 2,3-epoxy-pleuromutilintosylate is not depleted considering the 0.96% w/w 2,3-pleuromutilin epoxide input level in the commercial pleuromutilin batch.

Therefore it is highly desirable to have a pleuromutilin purification method available which significantly reduces 2,3-pleuromutilin epoxide and minimizes the likelihood of resulting impurities in the final active pharmaceutical ingredient (API).

The inventors recognized the fact that 2,3-pleuromutilin epoxide can result in API impurities by way of published data regarding tiamulin. In the EUROPEAN PHARMACOPOEIA 8.0 (page 3416 to 3418) the following tiamulin impurity I is listed:

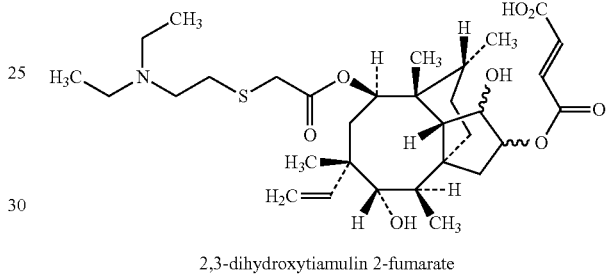

2,3-dihydroxytiamulin 2-fumarate

Tiamulin is presented as hydrogenfumarate salt. It is assumed that the impurity 2,3-dihydroxytiamulin 2-fumarate is most likely resulting from the reaction of a 2,3-epoxytiamulin impurity with fumaric acid.

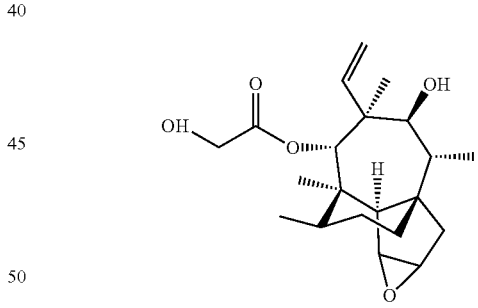

2,3-pleuromutilin expoxide

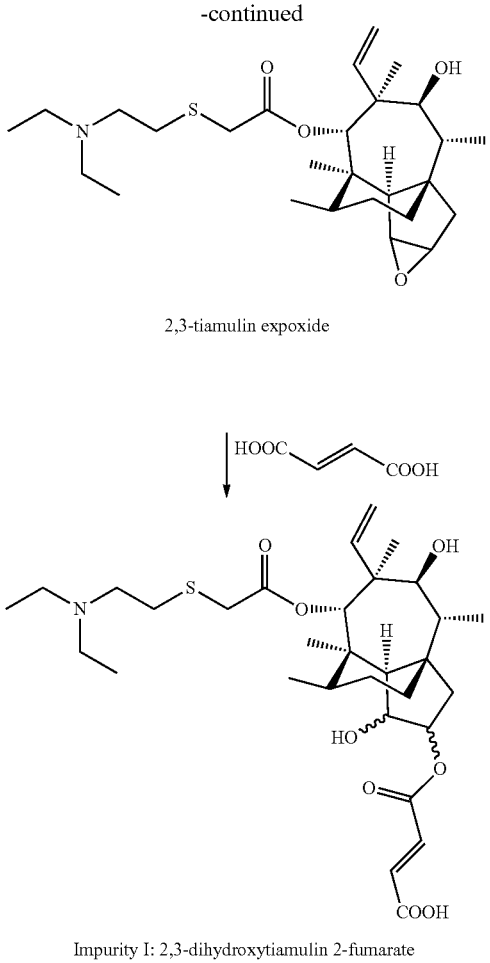

2,3-tiamulin expoxide

Impurity I: 2,3-dihydroxytiamulin 2-fumarate

The problem underlying the present invention is solved with a method for purifying pleuromutilin

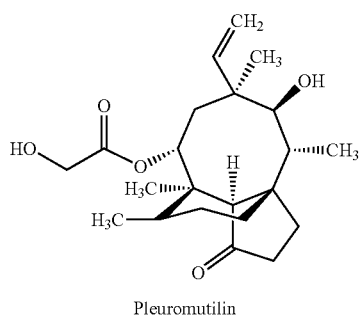 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin by means of crystallisation and/or recrystallisation in the presence of i-propylacetate.

Preferred embodiments of the present invention are defined in the dependent claims.

It has surprisingly been found that especially the amount of the impurity 2,3-pleuromutilin epoxide in pleuromutilin can be efficiently reduced by crystallising and/or re-crystallising pleuromutilin with i-propylacetate.

The term "crystallization and/or re-crystallization" comprises the following options:

A process wherein pleuromutilin is purified only via crystallization. In this case, i-propylacetate is present.

A process wherein pleuromutilin is purified via crystallisation and recrystallisation. In this case, at least in one of the two steps, preferably in both steps, i-propylacetate is present.

In a preferred embodiment of the present invention the process is performed by means of recrystallization, i.e. i-propylacetate is employed only in the recrystallization step.

The term "in the presence of i-propylacetate" means that other agents and, also, other solvents may be present in the crystallisation and/or recrystallisation process. Preferably, however, the solvent used in the crystallisation and/or re-crystallisation process essentially consists of i-propylacetate, i.e. no other solvent is present.

In a preferred embodiment of the present invention crystallisation and/or recrystallisation is carried out in the presence of an organic anti-solvent.

The concept of anti-solvent crystallization is well-known per se and means the addition of a liquid in which the compound to be purified is not or only slightly soluble (i.e. an "anti-solvent") to the solution of the compound in the crystallization solvent, so that the compound precipitation is promoted.

In a process of the present invention which comprises both a crystallisation and a re-crystallisation step, the anti-solvent should at least be present in the step or the steps of the process where i-propylacetate is present.

The skilled artisan is well aware of how to determine suitable anti-solvents for the solutions according to the process of the present invention, i.e. solutions of pleuromutilin in i-propylacetate.

Preferably, the anti-solvent is selected from the group consisting of heptane, hexane, and mixtures thereof.

In a preferred method according to any one of the preceding claims, crystallisation and/or re-crystallisation is carried out in the presence of a combination of i-propylacetate and an anti-solvent selected from the group consisting of:

i-propylacetate in the presence of heptane,
i-propylacetate in the presence of hexane,
and mixtures thereof.

The ratio of i-propylacetate to anti-solvent is preferably from 8 to 0.25, especially preferred 2 to 0.4.

The method of the present invention preferably comprises the step of employing seed crystals to initiate the crystallisation and/or recrystallisation.

The present application furthermore discloses a method for purifying pleuromutilin by means of crystallisation and/or recrystallisation in the presence of i-propylacetate or in the presence of i-propylacetate and anti solvent resulting in an overall purity of the obtained pleuromutilin of ≥95%, especially ≥97%.

Preferably, in this method the level of 2,3-pleuromutilin epoxide is reduced by 25% or more, more preferably 35% or more as compared with the level contained in the pleuromutilin before the crystallisation and/or recrystallisation step.

Especially, in this method the content of 2,3-pleuromutilin epoxide impurity is reduced from about 1.0% w/w to 0.70% w/w or even less in the obtained pleuromutilin.

DETAILED DESCRIPTION OF THE INVENTION

The trivial name mutilin refers to the IUPAC systematic name (1S, 2R, 3S, 4S, 6R, 7R, 8R, 14R)-3,6-dihydroxy-2,4,7,14-tetramethyl-4-vinyl-tricyclo[5.4.3.0$^{1,8}$]tetradecan-9-one.

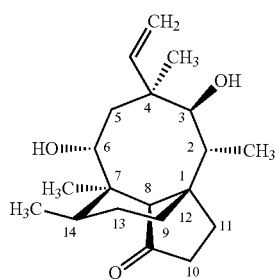

The present invention enables the purification of pleuromutilin and can be employed in the initial isolation/crystallisation after the product is extracted from the fermentation broth Alternatively, after the pleuromutilin has been isolated, a recrystallization can be performed using the solvents and solvent systems as specified above.

The pleuromutilin after isolating from fermentation has a reasonable high purity which can vary between about 85 to 95%. However, there is significant number of impurities present which are getting of concern if the pleuromutilin is used as starting material to produce semi-synthetic APIs for the treatment of animals or humans. In particular the presence of 2,3 pleuromutilin epoxide is of high concern.

In the tables below the purities of commercial (crude) pleuromutilin and purified pleuromutilin is presented.

| | Purified pleuromutilin batches after recrystallization using organic solvent/solvent systems | | | | | | |
|---|---|---|---|---|---|---|---|
| | Area % by HPLC | | | | | | |
| Impurity | Commercial pleuromutilin batch | Methyl-acetate (MeOAc) Procedure A | Ethyl-acetate (EtOAc) Procedure B | i-Propyl-acetate (i-PrOAc)* Procedure C | n-Propyl-acetate (n-PrOAc) Procedure D | i-Butyl-acetate (i-BuOAc) Procedure E | t-Butyl-acetate (t-BuOAc) Procedure F |
| 1 | 0.47 | 0.32 | 0.34 | 0.16 | 0.14 | 0.16 | 0.23 |
| 2 | 0.31 | 0.27 | 0.27 | 0.14 | 0.18 | 0.21 | 0.26 |
| 3 | 0.37 | n.d. | n.d. | n.d. | n.d. | n.d. | n.d. |
| 4 | 0.80 | n.d. | n.d. | n.d. | n.d. | n.d. | n.d. |
| 5 | 5.56 | 1.73 | 2.02 | 1.99 | 1.78 | 1.92 | 2.81 |
| 6 | 0.30 | n.d. | n.d. | n.d. | n.d. | n.d. | n.d. |
| 7 | 0.11 | n.d. | n.d. | n.d. | n.d. | n.d. | n.d. |
| 8 | 0.25 | n.d. | n.d. | n.d. | n.d. | n.d. | n.d. |
| 9 | 0.25 | n.d. | n.d. | n.d. | n.d. | n.d. | n.d. |
| 10 | 0.12 | n.d. | n.d. | n.d. | n.d. | n.d. | n.d. |
| 11 | 0.35 | n.d. | n.d. | n.d. | n.d. | n.d. | n.d. |
| 12 | 1.68 | n.d. | n.d. | n.d. | n.d. | n.d. | n.d. |
| 13 | 0.53 | n.d. | n.d. | n.d. | n.d. | n.d. | n.d. |
| 14 | 0.51 | n.d. | n.d. | n.d. | n.d. | n.d. | n.d. |
| 15 | 0.65 | n.d. | n.d. | n.d. | n.d. | n.d. | n.d. |
| 16 | 0.20 | n.d. | n.d. | n.d. | n.d. | n.d. | n.d. |
| 17 | 0.42 | n.d. | n.d. | n.d. | n.d. | n.d. | n.d. |
| Sum of other impurities below 0.10% area | 0.95 | 0.12 | 0.12 | 0.05 | 0.05 | 0.05 | 0.05 |
| Pleuromutilin purity | 86.17 | 97.56 | 97.25 | 97.66 | 97.85 | 97.66 | 97.56 |

*Example according to the present invention

In the following discussion the mutilin numbering system described by H. Berner (Berner, H.; Schulz, G.; Schneider H. *Tetrahedron* 1980, 36, 1807-1811) is used.

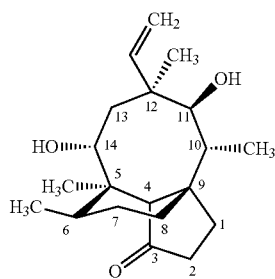

The present invention relates to efficient purification processes/methods by means of (re)-crystallisation of pleuromutilin.

| | Purified pleuromutilin batches after recrystallization using organic solvent/ anti solvent | | |
|---|---|---|---|
| | Area % by HPLC | | |
| Impurity | Commercial pleuro-mutilin batch | i-Propyl-acetate/ heptane (i-PrOAc/ heptane) isolated at room temperature* Procedure G | i-Propyl-acetate/ heptane (i-PrOAc/ heptane) isolated at 0 to 5° C.* Procedure H |
| 1 | 0.47 | 0.21 | 0.21 |
| 2 | 0.31 | 0.16 | 0.17 |
| 3 | 0.37 | n.d. | n.d. |
| 4 | 0.80 | n.d. | n.d. |
| 5 | 5.56 | 1.87 | 2.11 |
| 6 | 0.30 | n.d. | n.d. |
| 7 | 0.11 | n.d. | n.d. |
| 8 | 0.25 | n.d. | n.d. |
| 9 | 0.25 | n.d. | n.d. |
| 10 | 0.12 | n.d. | n.d. |
| 11 | 0.35 | n.d. | n.d. |
| 12 | 1.68 | n.d. | n.d. |

-continued

| | Purified pleuromutilin batches after recrystallization using organic solvent/anti solvent Area % by HPLC | | |
|---|---|---|---|
| Impurity | Commercial pleuromutilin batch | i-Propyl-acetate/heptane (i-PrOAc/heptane) isolated at room temperature* Procedure G | i-Propyl-acetate/heptane (i-PrOAc/heptane) isolated at 0 to 5° C.* Procedure H |
| 13 | 0.53 | n.d. | n.d. |
| 14 | 0.51 | n.d. | n.d. |
| 15 | 0.65 | n.d. | n.d. |
| 16 | 0.20 | n.d. | n.d. |
| 17 | 0.42 | n.d. | n.d. |
| Sum of other impurities below 0.10% area | 0.95 | 0.05 | 0.05 |
| Pleuromutilin purity | 86.17 | 97.71 | 97.46 | n.d.: not detected
*Examples according to the invention

The usage of hexane as anti-solvent, e.g. i-propylacetate/hexane leads to a comparable purification result.

As can be seen from the tables above with all purification methods applied, a significant purification is achieved.

After purification there are only three impurities remaining, with two of them being known impurities, namely 14-acetylmutilin and 2,3-pleuromutilin epoxide. The structure of 2,3-pleuromutilin epoxide has been elucidated by isolating the material from crude pleuromutilin and subjecting to analytical procedures like NMR and MS.

| | Structure | Relative Response Factor (RRF) to pleuromutilin at 210 nm detection wavelength in used HPLC method |
|---|---|---|
| Impurity 1 | Unknown | 1 |
| Impurity 2 2,3-Pleuromutilin epoxide | [structure] | 0.32 |
| Impurity 5 14-Acetylmutilin | [structure] | 0.96 |

The HPLC method to analyze the pleuromutilin batches is as follows:

| HPLC column | Phenomenex Kinetex C18 |
|---|---|
| Detection | 210 nm |
| Eluent A | 1 mL $H_3PO_4$ for HPLC + 1 L HPLC-Water |
| Eluent B | 1 mL $H_3PO_4$ for HPLC + 1 L Acetonitrile |
| Injection volume | 7 μL |

In order to determine the weight content of the impurities in the pleuromutilin, the area % values must be corrected with the Relative Response Factor (RRF) values for the impurities. Applying the response factor corrections leads to the following results for the two known impurities:

| | Impurity w/w % after response factor correction | | | |
|---|---|---|---|---|
| | 2,3-Pleuromutilin epoxide | | 14-Acetylmutilin | |
| Commercial and purified pleuromutilin batches after recrystallization using organic solvent/solvent systems | | reduction compared to commercial batch | | reduction compared to commercial batch |
| Commercial pleuromutilin batch | 0.96 | N/A | 5.79 | N/A |
| Methyl-acetate (MeOAc) | 0.84 | 12.5% | 1.80 | 68.9% |
| Ethyl-acetate (EtOAc) | 0.84 | 12.5% | 2.10 | 63.7% |
| i-Propyl-acetate (i-PrOAc)* | 0.44 | 54.1% | 2.08 | 64.0% |
| n-Propyl-acetate (n-PrOAc) | 0.56 | 41.7% | 1.85 | 68.0% |
| i-Butyl-acetate (i-BuOAc) | 0.66 | 31.2% | 2.00 | 65.5% |
| t-Butyl-acetate(t-BuOAc) | 0.81 | 15.6% | 2.93 | 49.4% |
| i-Propyl-acetate/heptane (i-PrOAc/heptane) isolated at room temperature* | 0.50 | 47.9% | 1.95 | 66.3% |
| i-Propyl-acetate/heptane | 0.53 | 44.8% | 2.20 | 62.0% |

| | Impurity w/w % after response factor correction | |
|---|---|---|
| | 2,3-Pleuromutilin epoxide | 14-Acetylmutilin |
| Commercial and purified pleuromutilin batches after recrystallization using organic solvent/solvent systems | reduction compared to commercial batch | reduction compared to commercial batch |
| (i-PrOAc/heptane) isolated at 0 to 5° C.* | | |

*Examples according to the invention

Surprisingly the reduction of the two known impurities is not the same for the series of acetic acid ester solvents used, optionally in the presence of an anti-solvent, to purify the commercial pleuromutilin batches. Most surprisingly the reduction of the critical 2,3-pleuromutilin epoxide is significantly enhanced when as crystallization solvent i-PrOAc, or a combination of i-PrOAc/heptane is used.

Especially, it is surprising that compared with n-PrOAc the reduction of the 2,3-pleuromutilin epoxide is still enhanced with i-PrAc in combination with an anti-solvent (heptane). This is surprising because while it is known that using an anti-solvent increases the yield of the process but tends to reduce the efficiency of the purification.

The above very surprising effects are very valuable in the further synthesis of semi-synthetic pleuromutilin derivatives. The reduction of 14-acetylmutilin is largely the same except for t-BuOAc where larger amounts are remaining in the pleuromutilin. However, as mentioned above, the impurity 14-acetylmutilin is not as important/critical as 2,3-pleuromutilin epoxide.

The impurity thresholds for APIs used in humans are very strict.

Drug substances for the human market have to fulfill the regulatory requirements defined in the corresponding ICH guidelines (International Conference on Harmonization of Technical Requirements for Registration of Pharmaceuticals for Human Use). The ICH guideline on impurities in new drug substances (Q3A(R2)) includes the following thresholds:

| Maximum daily dose | Reporting threshold | Identification threshold | Qualification threshold |
|---|---|---|---|
| <2 g | 0.05% | 0.10% | 0.15% |
| >2 g | 0.03% | 0.05% | 0.05% |

As can be seen from the ICH thresholds above it is desirable to have all individual unknown impurities below 0.10% area and the structure elucidated impurities below 0.15%, respectively. Pleuromutilin purification processes/methods provided according to the present invention supports to produce APIs (Active Pharmaceutical Ingredients) within the desired specifications and fulfilling ICH requirements.

It has been found that the (re)-crystallisation process according to the present invention is usable on large scale with high recoveries (in most cases >50%).

Of course, the (re-)crystallisation method according to the present invention can be repeated until the desired degree of purification is reached.

Abbreviations

API Active pharmaceutical ingredient
EP European Pharmacopoeia
g gram
kg kilogram
l liters
M molar
mmol millimolar
min minutes
ml milliliters
RRF Relative Response Factor
w/v weight/volume
w/w weight/weight Experimental Section—Pleuromutilin Purification Methods A) Solvent: Methyl Acetate Pleuromutilin (10.02 g, 26.5 mmol) and methyl acetate (20 ml) were charged to a flask and heated to 65° C. The batch was stirred at this temperature for 30 min to ensure dissolution, then cooled to 0-5° C. over 4 h, and stirred at this temperature for 1 h. The batch was then filtered, and the solid washed with cooled methyl acetate (10 ml) and dried in a vacuum oven at 40° C.

Yield: 6.70 g

B) Solvent: Ethyl Acetate

Pleuromutilin (10.07 g, 26.6 mmol) and ethyl acetate (20 ml) were charged to a flask and heated to 80° C. The batch was stirred at this temperature for 30 min to ensure dissolution, then cooled to 0-5° C. over 4 h, and stirred at this temperature for 1 h. The batch was then filtered, and the solid washed with cooled ethyl acetate (10 ml) and dried in a vacuum oven at 40° C.

Yield: 7.06 g

C) Solvent: Isopropyl Acetate—According to the Invention

Pleuromutilin (10.04 g, 26.5 mmol) and isopropyl acetate (20 ml) were charged to a flask and heated to 90° C. The batch was stirred at this temperature for 30 min to ensure dissolution, then cooled to 0-5° C. over 4 h, and stirred at this temperature for 1 h. The batch was then filtered, and the solid washed with cooled isopropyl acetate (10 ml) and dried in a vacuum oven at 40° C.

Yield: 5.83 g

D) Solvent: n-Propyl Acetate

Pleuromutilin (10.01 g, 26.4 mmol) and n-propyl acetate (20 ml) were charged to a flask and heated to 90° C. The batch was stirred at this temperature for 30 min to ensure dissolution, then cooled to 0-5° C. over 4 h, and stirred at this temperature for 1 h. The batch was then filtered, and the solid washed with cooled n-propyl acetate (10 ml) and dried in a vacuum oven at 40° C.

Yield: 4.64 g

E) Solvent: Isobutyl Acetate

Pleuromutilin (10.00 g, 26.4 mmol) and isobutyl acetate (20 ml) were charged to a flask and heated to 90° C. The batch was stirred at this temperature for 30 min to ensure dissolution, then cooled to 0-5° C. over 4 h, and stirred at this temperature for 1 h. The batch was then filtered, and the solid washed with cooled isobutyl acetate (10 ml) and dried in a vacuum oven at 40° C.

Yield: 6.43 g

F) Solvent: tert-Butyl Acetate

Pleuromutilin (10.00 g, 26.4 mmol) and tert-butyl acetate (20 ml) were charged to a flask and heated to 90° C. The batch was stirred at this temperature for 30 min but complete dissolution did not occur. The batch was cooled to 0-5° C. over 4 h, stirred at this temperature for 1 h, filtered, and the solid washed with cooled tert butyl acetate (10 ml). The solid product was then dried in a vacuum oven at 40° C.

Yield: 7.44 g

G) Solvent/Anti-solvent: Isopropyl Acetate/Heptane—Method 1—According to the Invention Pleuromutilin (10.01 g, 26.4 mmol) and isopropyl acetate (20 ml) were charged to a flask and heated to reflux to ensure dissolution. The batch was then cooled to 40-45° C. over 2 h. Heptane (40 ml) was then added dropwise over approximately 1 h, maintaining the temperature at 40-45° C. The batch was then stirred for 1 h at 40-45° C., cooled to room temperature over 1 h and stirred at this temperature for 1 h. The batch was then filtered, and the solid washed with cooled isopropyl acetate-heptane (1:1, 2×10 ml). The resulting solid was dried in a vacuum oven at 40° C.

Yield: 7.69 g

H) Solvent/Anti-solvent: Isopropyl Acetate/Heptane—Method 2—According to the Invention Pleuromutilin (10.01 g, 26.4 mmol) and isopropyl acetate (20 ml) were charged to a flask and heated to reflux to ensure dissolution. The batch was then cooled to 40-45° C. over 2 h. Heptane (40 ml) was then added dropwise over approximately 1 h, maintaining the temperature at 40-45° C. The batch was then stirred for 1 h at 40-45° C., cooled to room temperature over 1 h and stirred at this temperature for 1 h. The batch was then cooled to 0-5° C. over 1 h and stirred at this temperature for a further 1 h. The batch was then filtered, and the solid washed with cooled isopropyl acetate-heptane (1:1, 2×10 ml). The resulting solid was dried in a vacuum oven at 40° C.

Yield: 8.01 g

I) Pleuromutilin Tosylation

Pleuromutilin (10.03 g, 26.5 mmol) and acetonitrile (40 ml) were charged to a flask and a solution of sodium hydroxide (1.62 g, 40.5 mmol) in water (13.3 ml) was added, followed by acetonitrile (5 ml) as a line rinse. The batch was then cooled to 17° C. and p-toluenesulfonyl chloride (5.12 g, 26.9 mmol) was added, followed by acetonitrile (5 ml) as a line rinse. The batch was then stirred for 1.5 h at room temperature until complete by HPLC. Methyl tert-butyl ether (50 ml) and water (50 ml) were charged, stirred and allowed to settle. The lower aqueous layer was removed. The batch was then washed with 5% aqueous sodium chloride solution (2×50 ml). After separation and polish filtration, the batch was concentrated to approximately 6 vol, MTBE (100 ml) added and concentrated again to 6 vol. A further portion of MTBE (35 ml) was added and the batch concentrated to 6 vol. A mixture of diisopropyl ether (24 ml) and heptane (35 ml) was then added and the batch concentrated to 6 vol. A further mixture of diisopropyl ether (24 ml) and heptane (35 ml) was then added and the batch stirred for 30 mins. The batch was then heated to 57° C., stirred for 2 h and cooled to room temperature overnight before being filtered and washed with diisopropyl ether-heptane (2:3, 2×20 ml). The resulting solid was dried in a vacuum oven at 40° C.

Yield: 12.46 g

J) Solvent: Isopropyl Acetate with Seeding—Method 1—According to the Invention Pleuromutilin (200 g, 0.528 mol) and isopropyl acetate (400 ml) were charged to a flask and heated to reflux. The solution was stirred at reflux for 30 min. The batch was then cooled to 53° C. over 2 h, with pleuromutilin seeds (200 mg) added at 55° C. The batch was stirred for 2 h at 53° C., cooled to 20° C. over 2 h and stirred at this temperature for 2 h. The batch was then further cooled to 1° C. over 1 h and stirred at this temperature for a further 13 h. The batch was then filtered, and the solid washed with cooled isopropyl acetate (2×200 ml) and dried in a vacuum oven at 40° C.

Yield: 124.04 g

K) Solvent: Isopropyl Acetate with Seeding—Method 2—According to the Invention Pleuromutilin (200 g, 0.528 mol) and isopropyl acetate (400 ml) were charged to a flask and heated to reflux. The batch was stirred at reflux for 30 min to ensure dissolution, then cooled to 18° C. over 4 h, with pleuromutilin seeds (200 mg) added at 55° C. The batch was stirred for 2 h at 18° C., filtered, and the solid washed with cooled isopropyl acetate (2×200 ml) and dried in a vacuum oven at 40° C.

Yield: 106.59 g

L) Solvent/Anti-Solvent: Isopropyl Acetate/Hexane with Seeding—According to the Invention Pleuromutilin (200 g, 0.528 mol) and isopropyl acetate (400 ml) were charged to a flask and heated to reflux to ensure dissolution. The batch was then cooled to 45° C. over 3 h, with pleuromutilin seeds (60 mg) added after 2 h. The batch was then stirred for 1 h at 45° C., cooled to 17° C. over 2 h and stirred at this temperature for 12 h. The batch was then cooled to 5° C. over 1 h and stirred at this temperature for a further 2 h. Hexane (794 ml) was then added dropwise over approximately 4 h, maintaining the temperature at 5° C. The batch was then stirred at 5° C. for 2 h, filtered, and the solid washed with cooled isopropyl acetate (132 ml), followed by further cooled isopropyl acetate (66 ml), then cooled hexane (200 ml). The resulting solid was dried in a vacuum oven at 40° C.

Yield: 167.89 g

M) 2,3-Pleuromutilin Epoxide 2,3-pleuromutilin epoxide is isolated from pleuromutilin via a series of prep-HPLC separations. An initial purification was performed, followed by a second prep-HPLC separation to purify further. Finally, a third purification was carried out by SFC (Supercritical Fluid Chromatography) to provide the final 2,3-pleuromutilin epoxide.

In total about 7 g of 2,3-pleuromutilin epoxide were isolated from about 5 kg of bulk (crude) pleuromutilin with a purity >90%.

$^1$H-NMR (200 MHz, DMSO-d$_6$) δ 6.13 (dd, J$_{cis}$=10.8 Hz, J$_{trans}$=18.0 Hz, 1H, H-19), 5.58 (d, J=8.8 Hz, 1H, H-14), 5.25 (t, 1H, 22-OH), 5.05 (d, J$_{cis}$=13.2, 1H, H-20a), 5.01 (d, J$_{trans}$=9.2 Hz, 1H, H-20b), 4.46 (d, J=6.0Hh, 1H, 11-OH), 3.88 (AB, 2H, H-22), 3.60 (d, J=3.2 Hz, 1H, H-3), 3.32 (d, J=3.2 Hz, 1H, H-2), 3.23 (dd, 1H, H-11), 2.28-1.15 (11H, series of multiplets related to H1, H4, H6, H7, H8, H10 and H13), 1.18 (s, 3H H-15), 1.05 (s, 3H, H-18), 0.74 (d, J=7.2 Hz, 3H, H-17), 0.63 (d, J=6.8 Hz, 3H, H-16)

Mass Spec:
m/z=396.3 [M+H$_2$O]; m/z=423.5 [M+HCOO$^-$]

The invention claimed is:

1. A method for purifying pleuromutilin

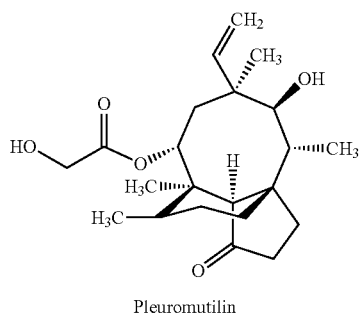 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin by means of crystallisation and/or recrystallisation in the presence of i-propylacetate.

2. A method according to claim 1 wherein crystallisation and/or recrystallisation is carried out in the presence of an organic anti-solvent.

3. A method according to claim 2, wherein said anti-solvent is selected from the group consisting of heptane, hexane, and mixtures thereof.

4. A method according to claim 1, wherein crystallisation and/or recrystallisation is carried out in the presence of a combination of i-propylacetate and an anti-solvent selected from the group consisting of:
 i-propylacetate in the presence of heptane,
 i-propylacetate in the presence of hexane, and
 mixtures thereof.

5. A method according to claim 2, wherein the ratio of i-propylacetate to anti-solvent is from 8 to 0.25.

6. A method according to claim 1, comprising the step of employing seed crystals to initiate the crystallisation and/or recrystallisation.

7. A method according to claim 2, wherein the ratio of i-propylacetate to anti-solvent is from 2 to 0.4.

8. A method according to claim 1, wherein the method removes pleuromutilin epoxide impurity.

9. A method according to claim 1, the method yielding pleuromutilin with a purity of ≥95%.

10. A method according to claim 1, the method yielding pleuromutilin with a purity of ≥97%.

11. A method for purifying pleuromutilin

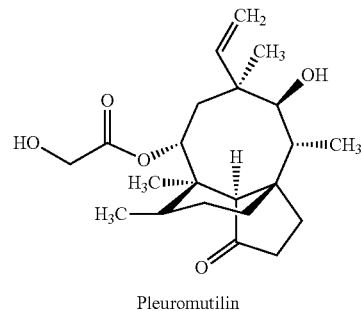 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin by means of crystallisation and recrystallisation in the presence of at least one solvent, wherein at least one of the crystallisation and the recrystallisation is in the presence of i-propyl acetate.

12. A method according to claim 11, the method yielding pleuromutilin with a purity of ≥95%.

13. A method according to claim 11, the method yielding pleuromutilin with a purity of ≥97%.

14. A method according to claim 11, further comprising employing seed crystals to initiate crystallisation and/or recrystallisation.

15. A method according to claim 1, wherein at least one of the crystallisation and recrystallisation is carried out in the presence of i-propyl acetate and heptane.

16. A method according to claim 1, wherein at least one of the crystallisation and recrystallisation is carried out in the presence of i-propyl acetate and hexane.

17. A method for purifying pleuromutilin

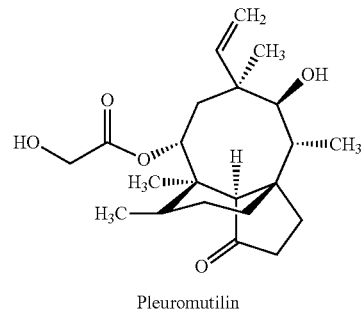 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin by means of crystallisation and recrystallisation in the presence of at least one solvent, wherein the crystallisation and the recrystallisation is in the presence of i-propyl acetate and an organic anti-solvent, the method yielding pleuromutilin with a purity of ≥95%.

18. A method according to claim 17, the method yielding pleuromutilin with a purity of ≥97%.

19. A method according to claim 17, wherein the organic anti-solvent comprises heptane.

20. A method according to claim 17, wherein the organic anti-solvent comprises hexane.

* * * * *

UNITED STATES PATENT AND TRADEMARK OFFICE
CERTIFICATE OF CORRECTION

PATENT NO. : 10,913,703 B2
APPLICATION NO. : 16/482809
DATED : February 9, 2021
INVENTOR(S) : Heilmayer et al.

It is certified that error appears in the above-identified patent and that said Letters Patent is hereby corrected as shown below:

In the Specification

Column 1
Lines 33-34, change "as crystalline" to –as a crystalline–

Column 3
Line 27, change "are using" to –use–

Column 4
Line 36, change "by submerged" to –by a submerged–

Column 6
Line 2, change "as significant" to –as a significant–

Column 10
Line 4, change "broth Alternatively" to –broth. Alternatively–
Line 15, change "is" to –are–

Column 13
Line 21, change "when as crystallization" to –when a crystallization–
Line 27, change "process but" to –process, but it–
Lines 58-59, change "supports to produce" to –facilitates production of–

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*